(12) United States Patent
Vernoy

(10) Patent No.: US 6,852,102 B1
(45) Date of Patent: Feb. 8, 2005

(54) DISPOSABLE ADULT UNDERGARMENT AFFORDING HIP PROTECTION

(76) Inventor: Terry Alan Vernoy, 2240 Kuhio Ave., Ph 3804, Honolulu, HI (US) 96815

( * ) Notice: Subject to any disclaimer, the term of this patent is extended or adjusted under 35 U.S.C. 154(b) by 23 days.

(21) Appl. No.: 10/618,137

(22) Filed: Jul. 11, 2003

Related U.S. Application Data

(63) Continuation-in-part of application No. 29/166,159, filed on Nov. 15, 2002, now Pat. No. Des. 485,355, and a continuation-in-part of application No. 29/166,160, filed on Nov. 15, 2002, now Pat. No. Des. 480,139.

(51) Int. Cl.$^7$ .............................................. A61F 13/15
(52) U.S. Cl. ............................ 604/385.31; 604/385.01; 604/385.12; 2/465; 2/467
(58) Field of Search ................................ 604/394, 396, 604/385.12, 385.31, 387, 385.01, 391, 385.03; 2/22, 23, 24, 455, 465, 228, 227, 267, 2.5, 69, 69.5, 247, 268, 243.1

(56) References Cited

U.S. PATENT DOCUMENTS

| | | | | |
|---|---|---|---|---|
| 3,801,984 A | * | 4/1974 | Kanicki | .......................... 2/459 |
| 3,909,847 A | | 10/1975 | Holt | |

(List continued on next page.)

FOREIGN PATENT DOCUMENTS

| | | | | |
|---|---|---|---|---|
| WO | WO98/08473 | * | 3/1998 | ............ A61F/13/15 |

OTHER PUBLICATIONS

Falls and Hip Fractures, AAOS Online Service Fact Sheet.
Acceptability and compliance with hip protectors in community-dwelling women at high risk of hip fracture, Rheumatology, Petal et al., 42 (6): 769.
Statistics Grim For Women's Hip Fractures, Virtual Hospt. www.vh.org.
Hip Fractures Are Major Health Concern Among Elderly, ibid.
Aging of the North American Population: New Challenges for Orthopaedics, J. of Bone & Joint Surgery, 2002–85–A No. 4.
Quality of life related to fear of falling and hip fracture in older women: a time trade off study, MI 2000: 320:341–34.

*Primary Examiner*—Jacqueline Stephens
(74) *Attorney, Agent, or Firm*—Godbey Griffiths Reiss

(57) ABSTRACT

A disposable adult diaper that protects against hip injuries, and in particular those resulting from impact to the bony prominence known as the greater trochanter, comprises a center panel that extends from the wearer's anterior waist, under the wearer's crotch, to the wearer's posterior waist, and ventral and dorsal wings that extend out from the center panel to cover the wearer's abdomen and backside, respectively. The ventral and dorsal wings are supplied with cushioning means and extend from the wearer's waistline to below the wearer's crotch line. The cushioning means can take the form of closely packed air filled cells, foam, or other shock-absorbing materials. The lateral aspects of the cushioned dorsal and ventral wings overlap one another and overlay the upper and lower bony prominence of the structures of the hip. The center panel may contain a moisture absorbent means to absorb moisture from human waste. Briefs and pull-ups having the same design and construction are also described.

10 Claims, 3 Drawing Sheets

U.S. PATENT DOCUMENTS

| | | | |
|---|---|---|---|
| 4,410,324 A | 10/1983 | Sabee | |
| 4,462,115 A | 7/1984 | Carlson | |
| 4,500,316 A | 2/1985 | Damico | |
| 4,718,901 A | 1/1988 | Singheimer | |
| 4,737,994 A | 4/1988 | Galton | |
| 4,854,989 A | 8/1989 | Singheimer | |
| 4,962,769 A | 10/1990 | Garcia | |
| 5,034,998 A | 7/1991 | Kolsky | |
| 5,157,789 A | 10/1992 | Klass | |
| 5,500,952 A | 3/1996 | Keyes | |
| 5,522,809 A | 6/1996 | Larsonneur | |
| 5,779,658 A | 7/1998 | Saca | |
| 5,868,725 A | 2/1999 | Coles | |
| 6,009,565 A | 1/2000 | Carrington | |
| 6,146,368 A * | 11/2000 | LaPointe | 604/385.26 |
| 6,408,446 B1 | 6/2002 | Carrington | |
| 2002/0078484 A1 | 6/2002 | Ulert | |
| 2002/0099346 A1 | 7/2002 | Strobl | |
| 2003/0093005 A1 | 5/2003 | Baker | |
| 2004/0015153 A1 * | 1/2004 | Strobl | 604/540 |

* cited by examiner

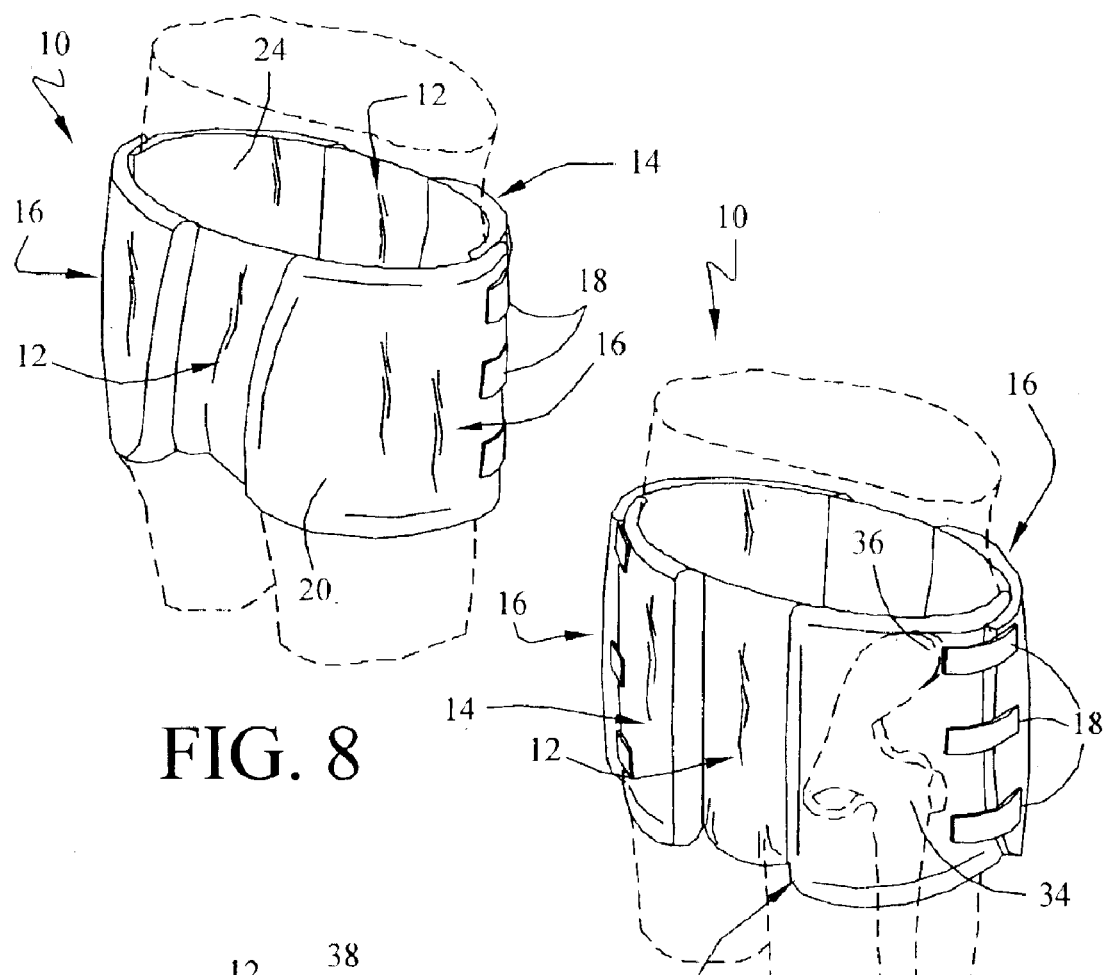
FIG. 8
FIG. 9
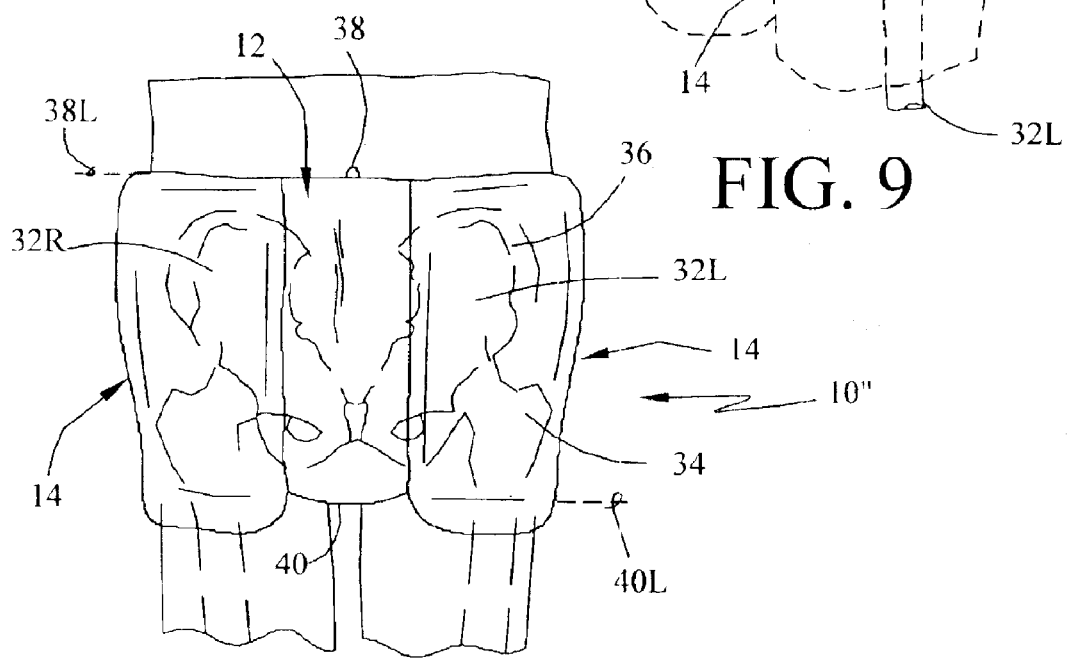
FIG. 10

DISPOSABLE ADULT UNDERGARMENT AFFORDING HIP PROTECTION

CROSS-REFERENCE TO RELATED PATENT APPLICATIONS

This is a utility patent application for a disposable adult undergarment which is a continuation-in-part and claims the benefit of, design patent applications Ser. No. 29/166,159 U.S. Pat. No. D,485,355 and Ser. No 29/166,160, U.S. Pat. No. D,480,139 both filed Nov. 15, 2002.

STATEMENT REGARDING FEDERALLY SPONSORED RESEARCH OR DEVELOPMENT

The subject invention is not the result of or in any way related to federally sponsored research or development.

BACKGROUND OF INVENTION

1. Field of Invention

The present invention relates to undergarments for the elderly. In particular, this invention describes a cushioned disposable undergarment that can function as a diaper or brief for the incontinent and which protects the wearer from hip injuries as a result of falls and trauma.

2. Description of the Prior Art

As health care has improved, and as the baby boomer generation matures, the United States increasingly finds itself with many more elderly people in need of health care services. Medical conditions suffered by our elderly, which are already depleting our health care dollars, can be expected to increase, possibly tenfold, leaving less resources available for medical care, with a far greater number of people requiring care. In particular, hospitalizations because of hip fractures among the elderly are expected to increase dramatically over the next three decades. J. Buckwalter et al., Aging of the North American Population: New Challenges for Orthopeadics, *J. of Bone & Joint Surgery* 2003; 85-A, No. 5.

In 1996, there were 340,000 hospitalizations resulting from hip fractures. Ibid. This number is expected to increase to 420,000 by the year 2020 and to 650,000 by the year 2050. American Academy of Orthopaedic Surgeons Online Service Fact Sheet, www.orthoinfo.aaso.org. The rate of hip fracture increases at age 50, doubling every five to six years. Ibid. Nearly half women over the age of 90 have suffered a hip fraction. Ibid.

Hip fractures are very expensive to treat. The cost of hip fracture care has been estimated at between $30,000 and $40,000 per fracture, and as much as $12 billion in medical care and lost income yearly. Virtual Hospital: Aging Begins at 30: 1999: Hip Fractures, www.vh.org. Only 25 percent of those who suffer hip fractures make a full recovery, and nearly 25 percent die within one year of sustaining the fracture. Ibid. The quality of life, particularly among older women, is significantly threatened by falls and by the fear of falling. G. Salkeld et al., Quality of life related to fear of falling and hip fractures in older women: a time trade off study, *BMJ* 2000; 320: 341–346.

As health care costs continue to increase, health care dollars and services are depleted, leading to the potential for rationing and compromising of health care services. Accordingly, there is an obvious need to prevent and/or decrease the number and seriousness of medical conditions, particularly those commonly suffered by the elderly, lessening, in turn, the need for health care dollars and services and allowing such dollars and services to be allocated to other health issues.

In the context of hip fracture prevention, what is needed is a cost efficient item that provides around-the-clock protection to elderly persons from hip fractures. Studies have shown that patients are protected from hip fractures if their momentum from a fall is broken by grabbing support or by hitting an object before landing. Virtual Hospital: Aging Begins at 30: 1999: Hip Fractures, www.vh.org. Similar results can be expected, and have been obtained, through the use of cushioning materials that overlays the bony structures of the hip and that function to absorb and disperse the energy that would otherwise be transmitted to the hip during a fall or other trauma. S. Patel et al. Acceptability and compliance with hip protectors in community-dwelling women at high risk of hip fracture, *Rheumatology,* 2003; 42 (6): 769 What is needed, then, is to provide an article that affords cushioning protection to the structures of the hip, as well as a method for obtaining compliance among the target population of regular use of such cushioning article.

Adult diapers are well known and understood, and a fair variety of such diapers are described in the patent and other literature and are commercially available. These diapers are, for the most part, intended to address the social and hygienic needs brought on by adult incontinence. As such, the available adult diapers include constructions and materials designed to absorb human waste and to keep the moisture from the waste away from the skin surface.

While the known adult diapers address the social and health issues caused by incontinence, and in at least one case include padding intended to protect against bed sores for those users restricted to bed, prior art adult diapers do not include designs, constructions and materials protecting the structures of the skeleton, and in particular the hip, from trauma resulting from falls. A primary object of the present invention is to provide an adult diaper that can be worn by the elderly, including those who are incontinent, to absorb human waste and keep moisture away from the wearer's skin, and which at the same time protects the wearer from hip trauma and fractures resulting from falls.

A number of published patents and patent applications teach undergarments, including briefs and panties, that incorporate special padding designed to protect the wearer from injury to skeletal structures including those of the hip and pelvis. U.S. Pat. No. 4,462,115 for example, by Carlson, et. al., describes a women's protective undergarment for volleyball. However such undergarments are not disposable and they do not take the form of diapers. While providing cushioning to skeletal prominence in the pelvic region, the Carlson and similar undergarments are more difficult to use, less efficient, and more expensive, as compared with undergarments that take the form of disposable diapers. Factors such as ease of use, disposability and cost hold particular importance to the elderly. Given the documented increasing high number of hip fractures among the elderly, despite the commercial availability of such protective undergarments, it is suspected that the acceptability and/or compliance of use of such undergarments among those most susceptible to hip fractures is poor at best. It is a further object of the present invention to provide a padded undergarment designed to protect bony prominence of the structures of the hip utilizing a diaper format that is easy and convenient to use, and that is sufficiently inexpensive to manufacture such that it can be used disposably.

Also found among the prior art are undergarments and diapers that include padding designed to protect the bony prominence of some of the structures that comprise the hip while leaving other bony prominence unpadded and exposed. It is well documented that the great majority of hip fractures are sustained through impact or trauma to that hip structure known as the greater trochanter. The greater trochanter projects out low among the hip structures, extending horizontally approximately in line with the crotch. Commercially available padded diapers and briefs, and the padded diapers and briefs described and depicted in publicly available literature, do not demonstrate cushioning means that overlay or that is capable of overlaying the greater trochanter. As a result, prior art diapers and briefs, those described in the literature and those available in the marketplace, cannot function to decrease the number and severity of hip injuries that result from trauma to the greater trochanter. It is a further object of the present invention to provide an adult diaper or brief that reduces the risk, number and severity of hip fracture by shielding or insulating the bony prominence of the hip, and in particular the greater trochanter, from trauma sustained during a fall.

BRIEF SUMMARY OF THE INVENTION

The foregoing and other objects are achieved in accordance with the present invention, a disposable adult diaper affording hip protection comprising a rectangular shaped center panel having two pairs of wings one each extending perpendicularly out from the bottom and top aspects, respectively, of the central panel and a detachable securing means affixed to the outside edges of at least one pair of wings. The wings incorporate a cushioning means, while the center panel may optionally incorporate a moisture absorbent material.

According to its preferred embodiment, the diaper wings of the present invention are generally rectangular in shape with inward facing edges that extend, in curvilinear fashion, towards one another. The wings demonstrate a height that approximates the distance between the wearer's umbilicus (bellybutton) and several inches below the crotch, and a width sufficient to extend beyond the wearer's flank and overlap the edge of the corresponding wing. The wings are spaced apart one from the other along the center panel by a distance that approximates the depth of the wearer's crotch.

The adult diaper of the present invention is worn by placing the center panel under the wearer's crotch, wrapping one pair of wings to encircle the wearer's backside and the other pair of wings to encircle the wearer's abdomen and pelvis, overlapping the outside edges of the first and second pair of wings, and detachably engaging the securing means to attach the outside edges of one pair of wings to the edges of the second pair of wings in overlapped fashion.

The height of cushioning wings will necessarily be large relative to the distance between the pairs of wings, usually by an order of at least three times. This, together with the right angle relationship between the wings and center panel, which combined characteristics are lacking among the padded diapers, panties and briefs described in the prior art literature, ensure that the lateral aspects of the cushioned wings overlay the bony prominence that corresponds to the greater trochanter, as well as the bony prominence that corresponds to the iliac crest of the pelvis. In this manner, the adult diaper of the present invention shields the two bony prominence most likely to sustain impact causing hip injuries and fractures.

The center panel may be layered with absorbent material bordered by sealing strips that function to absorb and contain moisture emanating from human waste for use with those who are incontinent. The diaper may also be constructed without layered absorbent material, resulting in a trimmer and less bulky diaper, for use with those who remain continent. The adult diaper of the present invention realizes all the conveniences and economies of a disposable diaper while at the same time achieving protection for those aspects of the hip most vulnerable to trauma.

According to an alternative embodiment, the outside edges of the wings of the present invention are permanently secured one to the other, providing a panty, brief or pull-up having all the same advantages and conveniences of the adult diaper of the present invention.

Further objects and advantages of this invention will become apparent from consideration of the drawings and ensuing description.

BRIEF DESCRIPTION OF THE DRAWINGS

FIG. 8 is a rear perspective view of the adult diaper of the present invention assembled and in use.

FIG. 9 is a front perspective transparent view of the adult diaper of the present invention assembled and in use the bony prominence that make up the left hip structure in relation to the cushioned wings of the diaper.

FIG. 10 is a front plan view of a further alternative embodiment of the present invention showing cushioned brief assembled and in use portraying in phantom view the bony prominence that make up the hip structure in relation to the cushioned wings of the brief.

DETAILED DESCRIPTION OF THE PREFERRED EMBODIMENTS

Figure 1:
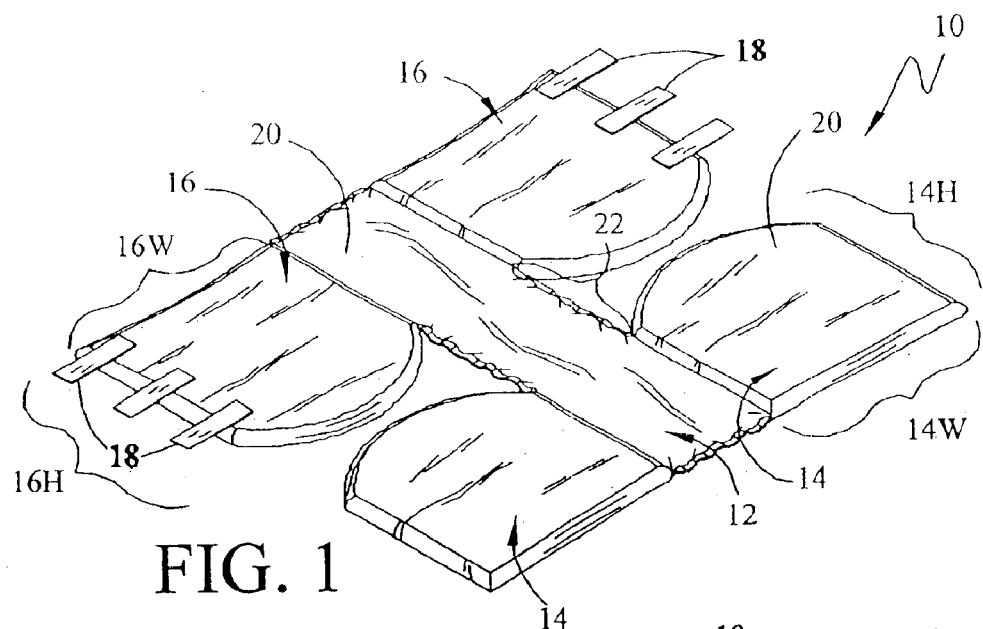
FIG. 1 is a perspective view of the outside of the adult diaper of the present invention in extended form.

A preferred embodiment 10 of the adult diaper of the present invention is depicted in extended form in FIG. 1. Diaper 10 comprises a center panel 12, a pair of ventral wings 14, and a pair of dorsal wings 16, both of which extend perpendicularly out from the top and bottom aspects, respectively, of center panel 12. A plurality of detachable securing means 18 project from the outside edges of dorsal wings 16. Covering both the center panel 12 and wings 14 and 16 of diaper 10 in a continuous manner is outside lining 20.

Center panel 12 is generally rectangular in shape as are ventral wings 14 and dorsal wings 16. According to the preferred embodiment depicted in FIG. 1, the inward facing edges of wings 14 and 16 are rounded to extend in curvilinear fashion towards one another. Also according to the preferred embodiment depicted in FIG. 1, dorsal wings 16 demonstrate a height 16H that is slightly larger than the height 14H demonstrated by ventral wings 14, while widths 14W and 16W of wings 14 and 16, respectively, are similar.

Relative to the intended user, height 14H measures the approximate distance between the user's umbilicus or waistline and several inches below the crotch or crotch line, and height 16H being slightly greater than this distance. Widths 14W and 16W measure a distance sufficient to extend the outside edges of wings 14 and 16 beyond the wearer's flank to overlap one another when wrapped around the wearer's flank. Wings 14 and 16 define a gap 22 along the outside edges of center panel 12. Gap 22 measures the approximate depth of the user's crotch. Heights 14H and 16H will necessarily be large relative to gap 22, typically by an order of at least three times.

Figure 2:
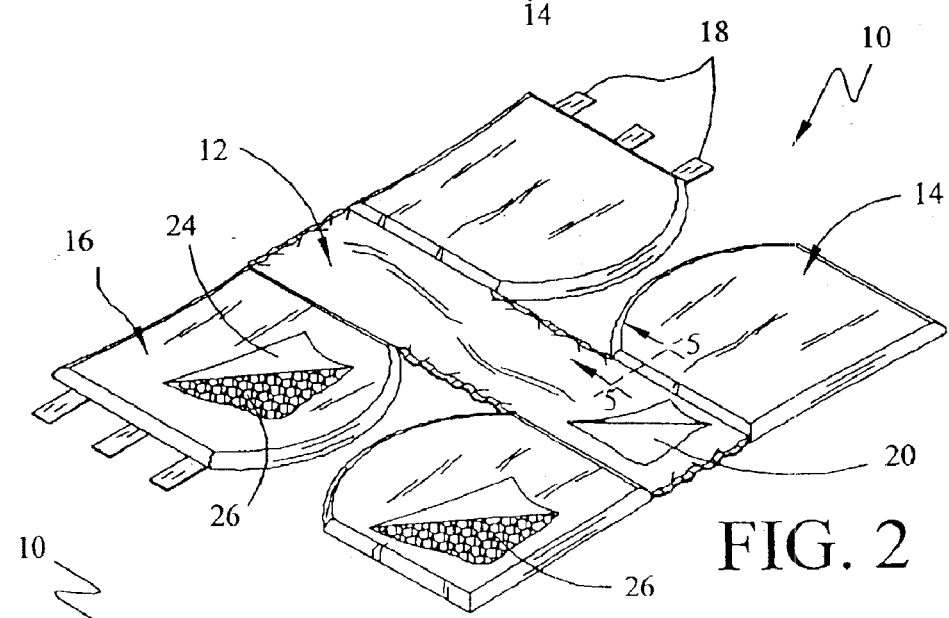
FIG. 2 is a perspective view of the inside of the adult diaper of FIG. 1 in extended form with a portion of the inside lining pealed away to reveal a cushioning means incorporated within the diaper wings and the absence of filler within the diaper center panel.

Adult diaper 10 is shown in extended form from the inside in FIG. 2, with portions of the diaper lining pealed away to reveal the lining contents. The inside view of diaper 10 is substantially identical to the outside view depicted in FIG. 1, comprising center panel 12, ventral wings 14, dorsal wings 16, and detachable securing means 18. According to this embodiment, detachable securing means 18 are shown as tabs projecting out from the back of the outside edges of dorsal wings 16, with adhesive applied to the inside of tabs 18. Detachable securing means 18 could also be affixed to extend out from ventral wings 14, or from both wings 14 and 16. Other known detachable fasteners, including hooks, buttons and the like, may be employed in lieu of tabs 18 providing similar results, without departing from the scope or spirit of the present invention.

An inside lining 24 covers center panel 12 and wings 14 and 16 in a continuous manner. Pealing away inside lining 24 from ventral wings 14 or dorsal wings 16 reveals a cushioning means sandwiched between inside lining 24 and outside lining 20. According to the preferred embodiment depicted, cushioning means 26 comprises a plurality of tightly packed air filled cells, one commercial embodiment of which is known as Bubble Wrap®. Pealing away inside lining 24 from center panel 12 reveals the inside of outside lining 20.

As shown in the embodiment of FIG. 2, outside lining 20 and inside lining 24 of adult diaper 10 is composed of the same material. While typically a viscoelastic plastic material, outside lining 20 and inside lining 24 can be fabricated from a variety of liner materials and can be made from the same material or different materials. As this diaper lacks moisture absorbent material within its center panel, it is intended for use by the continent in need of hip protection.

Figure 3:
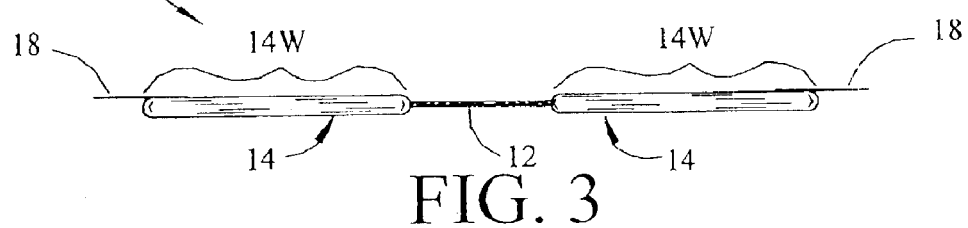
FIG. 3 is a view taken from the top or bottom of the adult diaper of FIG. 1 in extended form.

FIG. 3 illustrates adult diaper 10 in extended form viewed from the top or bottom. Ventral wings 14 extend out in a continuous manner from center panel 12. Because width 14W of ventral wings 14 approximately width 16W of dorsal wings 16, dorsal wings 16 are obscured from view in FIG. 3. Detachable securing means 18 project from the outside edges of dorsal wings 16.

Figure 4:
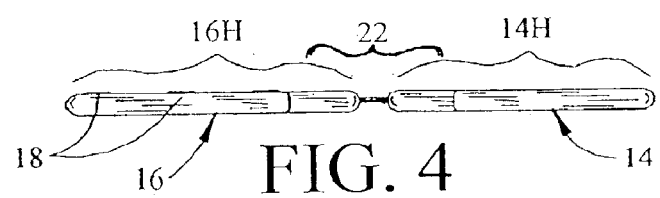
FIG. 4 is a view taken from the side of the adult diaper of FIG. 1 in extended form.

FIG. 4 is a side view of adult diaper 10 of the present invention in extended form. Wings 14 and 16 extend continuously out from center panel 12. Height 16H of dorsal wings 16 is slightly larger than height 14H of ventral wings 14, and heights 14H and 16H are several orders of magnitude larger than gap 22 between the inward facing edges of wings 14 and 16. Tabs 18 extend out from the back side of dorsal wings 16.

Figure 5:
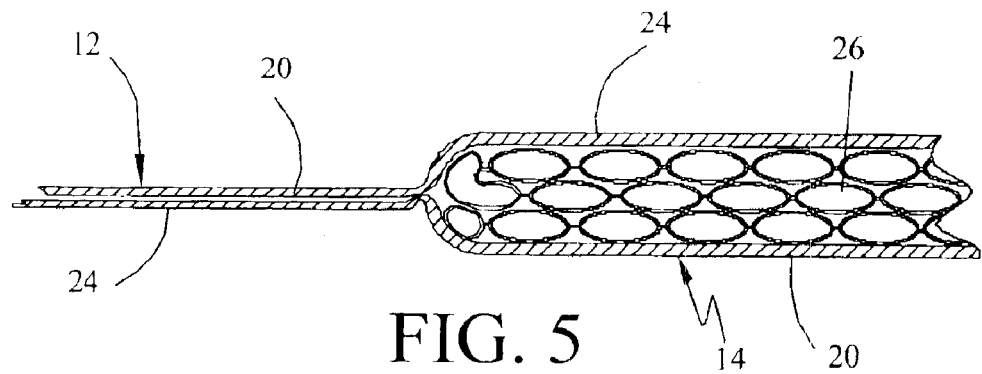
FIG. 5 is a cross-sectional view of a portion of the adult diaper of FIG. 1 taken along line 5—5 of FIG. 2, showing a cushioning means comprising a plurality of air-filled sacks.

A cross-section of portions of the adult diaper 10 of the present invention, taken along line 5—5 of FIG. 2, is depicted in FIG. 5. A cushioned wing, here labeled ventral wing 14 but which could alternatively be dorsal wing 16, is comprised of cushioning means 26 sandwiched between inside lining 24 and outside lining 20. Cushioning means 26 consists of tightly packed air-filled cells. Center panel 12 of the illustrated embodiment comprises inside lining 24 and outside lining 20 lying adjacent to one another. Linings 20 and 24 overlay, in a continuous manner, center panel 12 and wings 14 and 16.

Figure 6:
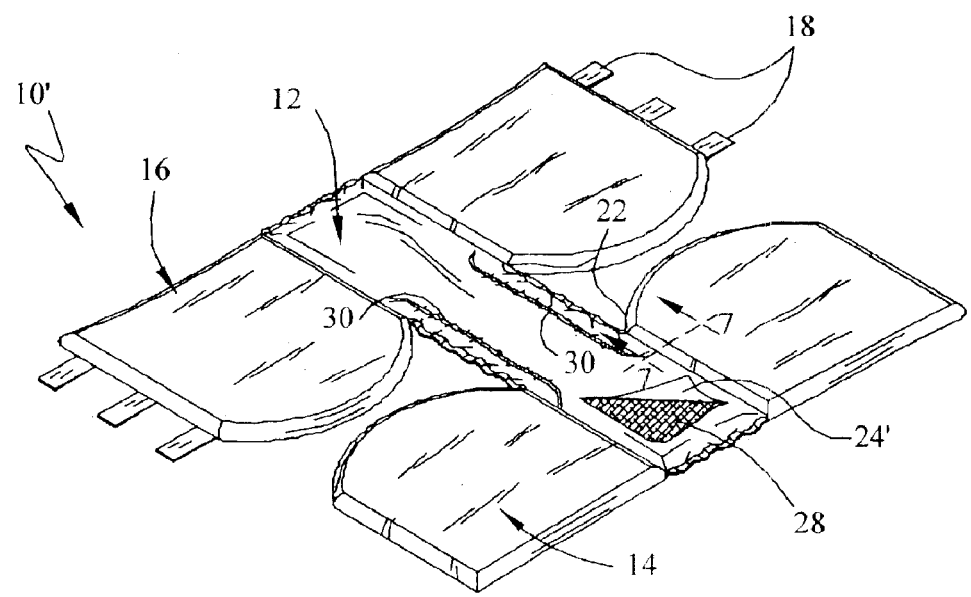
FIG. 6. is a perspective view of the inside of an alternative preferred embodiment of the adult diaper of the present invention in extended form with a portion of the inside lining pealed away to reveal a cushioning means incorporated within the diaper wings and an absorbent material incorporated within the diaper center panel.

A perspective view of the inside of an alternative embodiment adult diaper 10' in extended form is illustrated in FIG. 6, with lining of center panel 12 pealed away to reveal its contents. Like diaper 10, alternative embodiment diaper 10' comprises center panel 12, wings 14 and 16 extending continuously out from center panel 12 and perpendicular thereto, securing tabs 18 and inside lining 24'. Unlike diaper 10, adult diaper 10' includes a moisture absorbent means 28 sandwiched in between linings 20 and 24. Adult diaper 10' also includes a pair of sealer strips 30 along the lateral aspects of center panel 12, bordering and extending just beyond either side of gap 22.

Alternative embodiment adult diaper 10' is intended for use by the incontinent and collects moisture from human waste within center panel 12. Inside lining 24' is fabricated from a liquid permeable material to allow moisture deposited by the user to be absorbed through liner 14' into absorbent means 28. Sealer strips 30, which are fabricated from a liquid impermeable material and which may be elastic or viscoelastic, keep the absorbed moisture contained in absorbent means 28 from leaking out the sides. Absorbent means 28 can be cotton, water absorbent polymers, or any of a variety of moisture absorbing natural and synthetic materials commonly employed in commercially disposable diapers.

Figure 7:
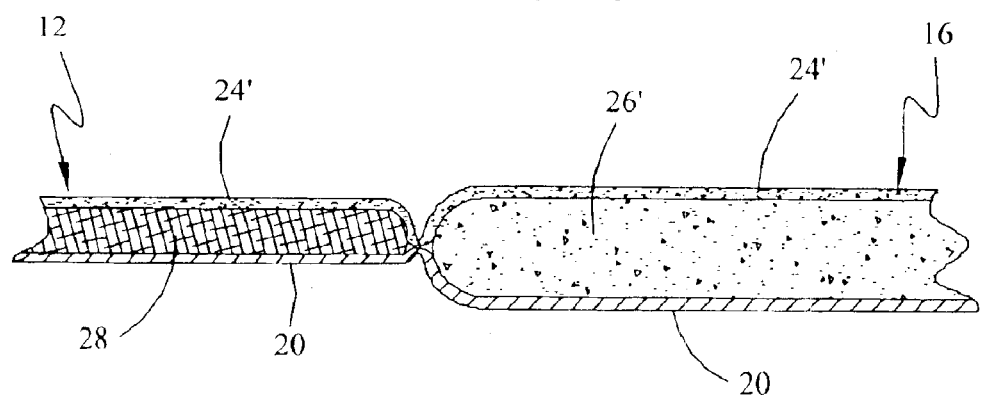
FIG. 7 is a cross-sectional view of a portion of the alternative embodiment adult diaper of FIG. 6 taken along line 7—7 of FIG. 7.

A cross-section of portions of the alternative embodiment adult diaper 10' of the present invention, taken along line 7—7 of FIG. 6, is depicted in FIG. 7. A cushioned wing, here labeled dorsal wing 16 but which could alternatively be ventral wing 14, is comprised of a cushioning means 26' fabricated from foam sandwiched between a moisture permeable inside liner 24' and a moisture impermeable outside liner 20. Center panel 12 of preferred embodiment diaper 10' is comprised of moisture absorbent means 28 sandwiched between inside lining 24' and outside lining 20. Linings 20 and 24' overlay, in a continuous manner, center panel 12 and wings 14 and 16.

While inside lining 24' is composed of a moisture permeable material such as fabric, outside lining 20 is made from a moisture impermeable material such as plastic or viscoelastic plastic. In this manner, moisture excreted by the wearer can be absorbed through inside liner 24' into absorbent means 28 within center panel 12. The moisture is prevented from leaking out from the back of center panel 12 by moisture impermeable outside liner 20, and is prevented from leaking out from the sides of center panel 12 by sealer strips 30 (depicted in FIG. 6).

The cushioning means 26' depicted in FIG. 7 is foam. It will be appreciated by those schooled in the pertinent industry that cushioning means 26 is not limited to air filled sacks and foam. Cushioning means 26 can also take the form of Tempur®, a pressure-relieving material having a cellular structure originally developed by NASA, tightly packed liquid filled cells, and a variety of known and commercial available materials capable of absorbing shock and dissipating kinetic energy. Utilizing these alternative materials will obtain similar results, without departing from the scope or spirit of the present invention.

FIG. 8 is a rear view of adult diaper 10 assembled and in use on a wearer. Diaper 10 is assembled about the wearer by placing center panel 12 under and through the wearer's crotch with inside lining 24 facing upward against the wearer. Ventral wings 14 are wrapped around the wearer's abdomen and pelvic regions, while dorsal wings 16 are wrapped around the wearer's backside. The lateral aspects of wings 16 overlap and overlay the lateral aspects of wings 14. Attaching means 18 then detachably secures wings 16 to wings 14.

As assembled on the wearer, the top edge of diaper 10 is substantially horizontal and approximately even with the wearer's umbilicus or waist line. The bottom edge of diaper 10 is similarly substantially horizontal and extends below the wearer's crotch or crotch line by approximately three to four inches. Cushioned wings 14 and 16 are thereby positioned to provide protection along the length of the wearer's flank from a point extending horizontally from the wearer's umbilicus to a point extending a few inches below the wearer's crotch.

The manner in which diaper 10 overlays and protects the bony prominence of the hip is illustrated in FIGS. 9 and 10. FIG. 9 is a front perspective view of diaper 10 shown in relation to the bony structures of the wearer's left hip 32L. Protruding from left hip structure 32L are two bony prominence, the greater trochanter 34, a bony prominence of the femur bone, and the iliac crest 26, being a bony prominence of the pelvic bone. Greater trochanter 34 extends low on the hip just above or approximately in line with the crotch. Iliac crest 36 extends high on the pelvis just below the umbilicus. The lower lateral aspects of wings 14 and 16 overlay greater trochanter 34 while the upper lateral aspects of wings 14 and 16 overlay iliac crest 36. Dorsal wings 16 overlap ventral wings 14 along the wearer's flank, affording a double layer of cushioning along that length of the flank most vulnerable to trauma that typically results in hip fractures among the elderly.

FIG. 10 is a front plan view of a further alternative embodiment of the undergarment of the present invention in the form of a cushioned brief 10", shown in relation to the bony structures of left hip 32L and right hip 32R. Center panel 12 surrounds the wearer's crotch. Ventral wings 14 are seen extending along the wearer's flank from a point approximately even with the wearer's umbilicus 38, to wit the wearer's waistline 38L, to a point extended several inches below the wearer's crotch 40 and crotch line 40L. Due to the dimensions of wings 14 and 16 relative to the wearer and to central panel 12, the top and bottom edges of wings 14 and 16 (obscured in FIG. 10 but visible in FIGS. 8 and 9) extend out horizontally from umbilicus 38 and from below crotch 40. The top and bottom aspects of wings 14 and 16 overlay greater trochanter 34 and iliac crest 36. The overlapping lateral aspects of wings 14 and 16 lie atop these bony prominence, providing a double layer of protection from shock and trauma.

While the hip protecting undergarments of the present invention have been described and depicted in the form of an adult diaper with wings 14 and 16 detachably secured to one another, adult brief 10" is formed by permanently securing dorsal wings 16 to ventral wings 14. Panties, panty briefs and/or pull-ups that provide the same quantity and quality of hip protection and most of the same conveniences as the disposable diaper described previously can be constructed in like manner. As with the disposable diapers of the present invention, the cushioned wings of the hip protecting brief 10" or similarly constructed pull-up overlay the wearer's flanks from a point along the wearer's waistline to a point below the wearer's crotch line. Though permanently secured, the cushioned wings can be overlapped to double the thickness of cushioning along those regions most in need of protectiong against shock. Brief 10"'s center panel can contain absorbent material for the incontinent, or consist of adjoining linings for others. Though somewhat more cumbersome to put on and take off for those with restricted mobility, the hip protecting briefs and pull-ups of the present invention may be preferred by others. Offering a variety of hip protecting undergarments demonstrating the design and construction of the present invention serves to maximize user compliance and the consequent prophylaxis against hip fracture.

SUMMARY AND SCOPE

Accordingly, it will be appreciated that the disposable adult diaper of the present invention addresses the personal hygiene needs of the elderly, particularly those who are incontinent, while placing the wearer at a significantly decreased risk of sustaining hip fractures.

Widespread use of the claimed invention has the potential to save significant health care dollars by preventing devastating hip fractures from falls sustained at home, in a nursing or care home, or in a hospital. The diaper may decrease the total number of hip fracture cases in the United States, notwithstanding the increasing number of people who are at risk for such injuries, e.g., the elderly, stroke victims, those with Parkinson's, etc. Significant savings would also be realized by limiting the potential of litigation that results from such injuries, thereby allowing health care dollars to be directed to better uses.

The diaper of the present invention is light weight, disposable, affordable, dependable and economical. It is a practical product that is easy to use and apply, predicting a high degree of patient compliance through regular use and changing of the diaper. Because the adult diaper of the present invention must necessarily be discarded after being soiled, proper use of the diaper through regular changing is assured.

Many patients in nursing or care homes, in hospitals or receiving home care are already using adult diapers. The adult diaper of the present invention is a practical way of continuing to provide incontinence care, while also preventing a possible devastating hip fracture. The adult diaper affording hip protection can further improve the quality of life of the elderly by decreasing the fear of falling and sustaining a hip fracture. The protection furnished by the diaper of the present invention affords peace of mind to family members, who will appreciate that they have supplied their loved ones with a product that can protect them from serious and devastating injury so often experienced by the elderly.

Although the description of the various embodiments of the present invention have been set forth with specificity, it is contemplated that modifications could be made without departing from the spirit and scope of the present invention. Accordingly, the scope of the invention should be determined by the appended claims and their legal equivalents, rather than with reference to any particular example, embodiment or illustration.

The embodiments of the invention in which an exclusive property or privilege is claimed are defined as follows:

1. An adult undergarment affording hip protection comprising
    a rectangular shaped center panel that extends from the wearer's anterior waist, through and under the wearer's crotch, to the wearer's posterior waist;
    ventral wings containing cushioning means that extend out from said center panel, perpendicular thereto, to cover the wearer's abdomen and pelvis region from the wearer's waistline to below the wearer's crotch line;
    dorsal wings containing cushioning means that extend out from said center panel, perpendicular thereto, to cover the wearer's backside from the wearer's waistline to below the wearer's crotch line;
    wherein the lateral aspects of said cushioned dorsal and ventral wings overlap and overlay the upper and lower bony prominence of the structures of the hips.

2. The adult undergarment of claim 1 wherein the lateral aspects of said ventral and dorsal wings can be detachably fastened one to the other to provide a diaper.

3. The adult undergarment of claim 2 wherein the detachable fastening means is a plurality of tabs having adhesive on one side that extend from the lateral aspects of said dorsal or ventral wings.

4. The adult undergarment of claim 1 wherein the inside facing edges of said ventral wings and dorsal wings extend towards one another in curvilinear fashion.

5. The adult undergarment of claim 1 wherein said ventral wings and dorsal wings extend below the wearer's crotch line by at least 2 inches.

6. The adult undergarment of claim 1 wherein said cushioning means is selected from a group consisting of closely packed air filled cells, closely packed liquid filled cells, viscoelastic memory cells, and foam.

7. The adult undergarment of claim 1 further comprising a moisture absorbing means within said center panel to absorb moisture from human waste.

8. The adult undergarment of claim 7 further comprising a liquid impermeable lining covering the undergarments outside and a liquid permeable lining covering the undergarments inside.

9. The adult undergarment of claim 8 wherein said liquid impermeable lining is fabricated from a viscoelastic plastic material.

10. The adult undergarment of claim 7 further comprising sealing strips affixed along the lateral aspects of said center panel to prevent moisture leakage.

* * * * *